United States Patent [19]

Kanai

[11] Patent Number: 5,217,429
[45] Date of Patent: Jun. 8, 1993

[54] APPARATUS FOR DRIVING BLOOD PUMPING DEVICE
[75] Inventor: Naritoshi Kanai, Anjo, Japan
[73] Assignees: Aisin Seiki Kabushiki Kaisha, Kariya; Kabushiki Kaisha Shinsangyokaihatsu, Tokyo, both of Japan
[21] Appl. No.: 653,411
[22] Filed: Feb. 11, 1991
[30] Foreign Application Priority Data Feb. 20, 1990 [JP] Japan .................................. 2-39009

[51] Int. Cl.⁵ .................................. A61N 1/362
[52] U.S. Cl. .................................. 600/18; 623/3
[58] Field of Search .................................. 600/16-18; 128/672, 673, 675; 604/96, 99; 623/3

[56] References Cited
U.S. PATENT DOCUMENTS 4,175,264 11/1979 Schiff .
4,832,005 5/1989 Takamiya et al. .................. 600/18
4,974,774 12/1990 Nakagawa et al. ................. 600/18
5,045,051 9/1991 Milder et al. ........................ 600/18

Primary Examiner—Lee S. Cohen
Assistant Examiner—John P. Lacyk
Attorney, Agent, or Firm—Burns, Doane, Swecker & Mathis

[57] ABSTRACT

An apparatus capable of automatically exchanging helium gas filling a balloon pump inserted in the aorta of a patient. The apparatus comprises a pressure generator producing positive pressure and negative pressure, an electronic control unit, an electrocardiograph, and a helium supply and discharge device. The positive and negative pressures produced by the pressure generator are alternately supplied to the balloon pump. The timer measures the time for which the pressure generator operates. The electronic control unit operates in response to the output signal from the timer and exchanges the helium gas with new helium gas whenever the the pressure generator operates the balloon pump for about 2 hours.

5 Claims, 4 Drawing Sheets

APPARATUS FOR DRIVING BLOOD PUMPING DEVICE

FIELD OF THE INVENTION

The present invention relates to an apparatus for driving a so-called blood-pumping device such as an artificial heart or a balloon pump inserted in the main artery and, more particularly, to a driving apparatus capable of automatically exchanging shuttle gas which would have heretofore been replaced on a doctor's judgement.

BACKGROUND OF THE INVENTION

It is known that the pulsating pressure of blood delivered from the heart of a person has a completely rectangular waveform. Preferably, therefore, the driving apparatus switches the pressure from positive pressure to negative pressure and vice versa at high speeds in order that the pulsating pressure of blood delivered from a blood-pumping device approach a rectangular waveform as close as possible.

The speed at which the pressure is switched from positive pressure to negative pressure or vice versa increases as the mass of the shuttle gas filling the inside of the blood-pumping device decreases. For this reason, it is desired to use helium gas or other gas having small mass as the shuttle gas. As an example, U.S. Pat. No. 4,175,264 issued Nov. 20, 1979 discloses a driving apparatus that uses helium gas as the shuttle gas.

In a blood-pumping device, the shuttle gas is separated from blood by a thin membrane and so the water vapor contained in the blood dissolves into the shuttle gas through the membrane. This increases the mass of the shuttle gas. Also, the water vapor dissolved in the shuttle gas changes into droplets of water, thus hindering movement of the shuttle gas.

Therefore, it is the common practice to stop the blood-pumping device for a short time on a doctor's or nurse's judgement. Then, water gathering in the blood-pumping device is removed by the doctor or nurse. In order to maintain the performance of the blood-pumping device, the removable of water has been required heretofore. For this purpose, the doctor must constantly monitor the device.

SUMMARY OF THE INVENTION

It is an object of the invention to provide a driving apparatus which makes it unnecessary for a doctor or nurse to remove water.

The above object is achieved by a driving apparatus comprising a water vapor amount-measuring means for detecting the amount of the water vapor contained in shuttle gas and a shuttle gas-exchanging means which exchanges the shuttle gas with new gas when the water vapor amount-measuring means detects a given amount of water vapor.

In this driving apparatus, as the amount of the water vapor contained in the shuttle gas increases, the gas is replaced with new gas. Therefore, the amount of the water vapor contained in the shuttle gas is suppressed. Consequently, the increase in the mass of the shuttle gas is suppressed, and only a small amount of water droplets is produced. In this way, it is unnecessary for a doctor or nurse to remove water.

Other objects and features of the invention will appear in the course of the description thereof which follows.

DETAILED DESCRIPTION OF THE INVENTION

Figure 3:
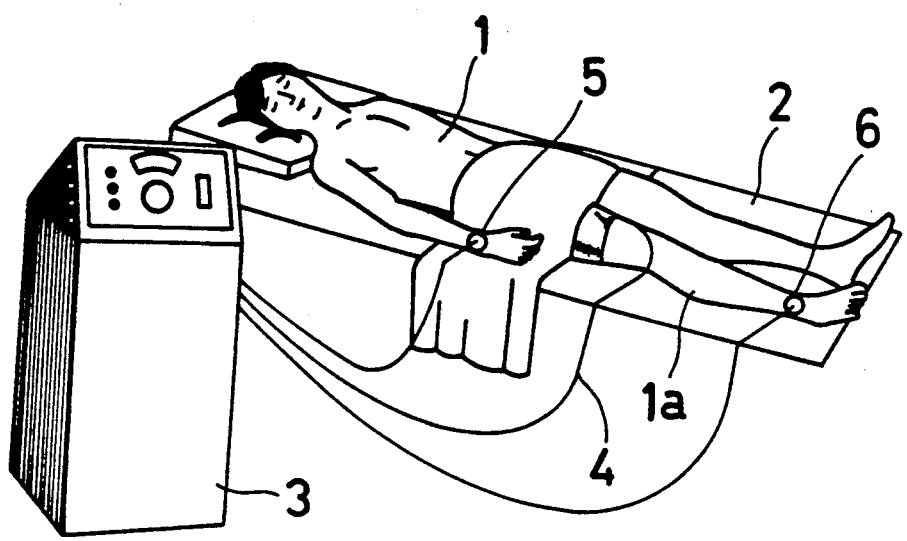
FIG. 3 is a perspective view of a medical bed and a patient who is being cured, using a balloon pump inserted in the main artery.

Referring to FIG. 3, a patient 1 lying down on a medical bed 2 is cured with a balloon pump 4 inserted in the aorta. An apparatus 3 for driving a blood-pumping device is installed close to the bed 2. The balloon pump 4 is connected with the driving apparatus 3. The pump 4 is inserted into the body of the patient 1, or a descending portion of the aorta, from one foot 1a of the patient 1. The manner in which the balloon pump 4 is inserted into the body of the patient 1 has been already introduced by many papers and is known. Therefore, the method of insertion is not described in detail herein. The pump 4 can be inserted into the body of the patient 1 by the Seldinger's method, for example. Electrodes 5 and 6 are attached to the patient 1 to observe an electrocardiogram.

Figure 1:
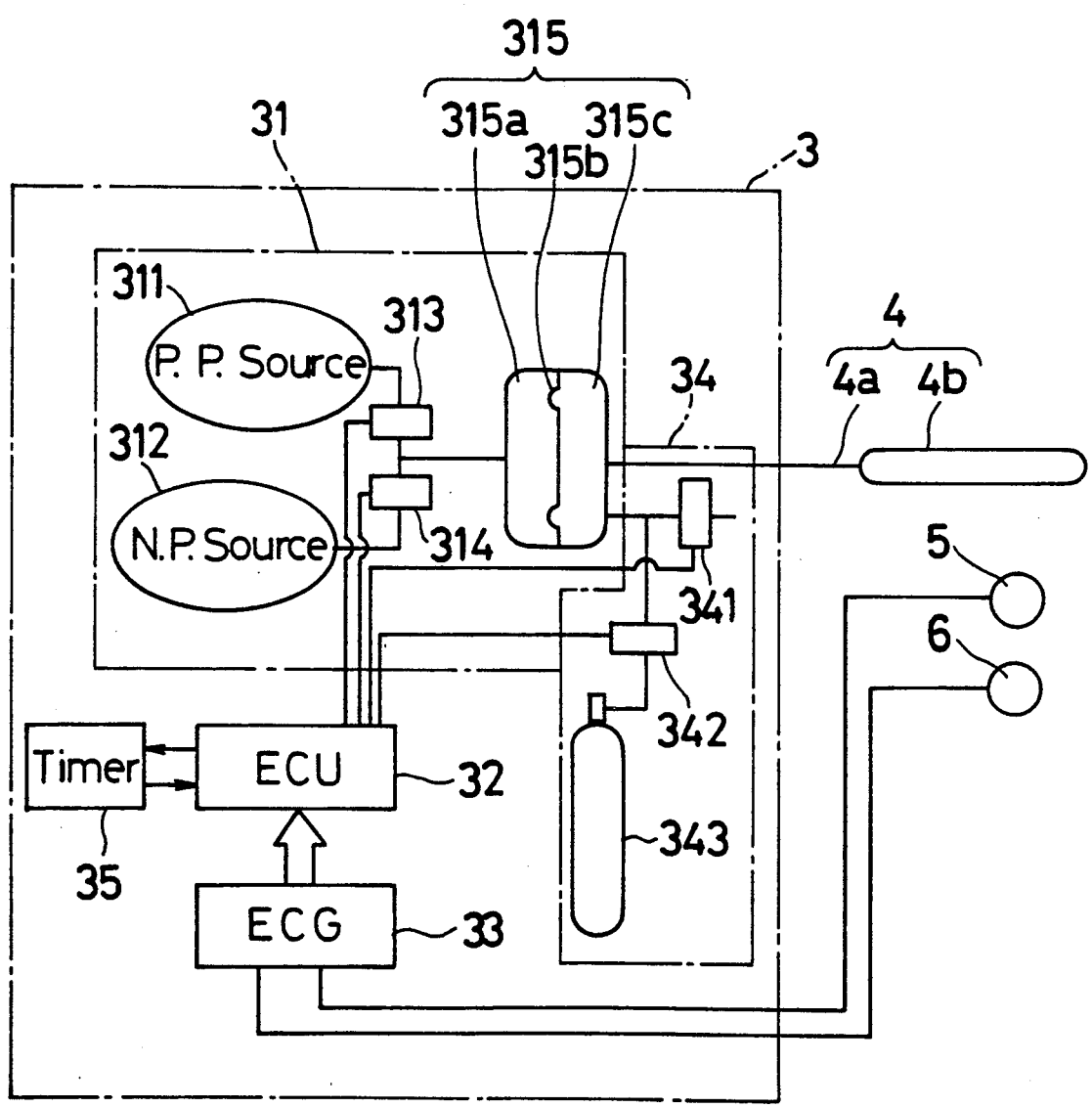
FIG. 1 is a block diagram of a driving apparatus according to the invention.

The driving apparatus 3 embodying the concept of the invention is next described by referring to FIG. 1. The balloon pump 4 consists of a tubular portion 4a connected with the driving apparatus 3 and a balloon portion 4b which expands and contracts in the aorta. The driving apparatus comprises a pressure generator 31 for supplying positive pressure and negative pressure alternately to the pump 4, an electronic control unit 32, an electrocardiograph 33, a device 34 for supplying and discharging helium, and a timer 35.

The pressure generator 31 comprises a positive pressure source 311, a negative pressure source 312, a positive pressure-switching valve 313, a negative pressure-switching valve 314, and an isolator 315. The isolator 315 comprises a primary chamber 315a, a secondary chamber 315c, and a movable membrane 315b separating these chambers from each other. The primary chamber 315c is filled with air. The secondary chamber 315c is filled with a shuttle gas. In the present example, helium gas is used as the shuttle gas.

The positive pressure-switching valve 313 and the negative pressure-switching valve 314 are connected with the primary chamber 315a. When the positive pressure-switching valve 313 is opened and the negative pressure-switching valve 314 is closed, positive pressure is introduced into the primary chamber 315a from the positive pressure source 311. At this time, the movable membrane 315b is displaced toward the secondary chamber 315c to expand the balloon portion 4b of the pump 4. Conversely, when the negative pressure-switching valve 314 is opened and the positive pressure-switching valve 313 is closed, negative pressure is admitted into the primary chamber 315a from the negative pressure source 312. At this time, the movable membrane 315b is displaced toward the primary chamber 315a to cause the ballon portion 4b of the pump 4 to contract. The switching valves 313 and 314 are opened and closed by the electronic control unit 32 which operates in response to the output signal from the electrocardiograph 33.

The device 34 for supplying and discharging helium is connected with the secondary chamber 315c and comprised of an exhaust valve 341, a supply valve 342, and a helium tank 343. When the exhaust valve 341 is opened, the secondary chamber 315c is exposed to the atmosphere, thus permitting the shuttle gas to be expelled to the atmosphere. Conversely, when the supply valve 342 is opened, the shuttle gas is supplied into the secondary chamber 315c from the helium tank 343. The valves 341 and 342 are opened and closed by the electronic control unit 32.

Figure 2A:
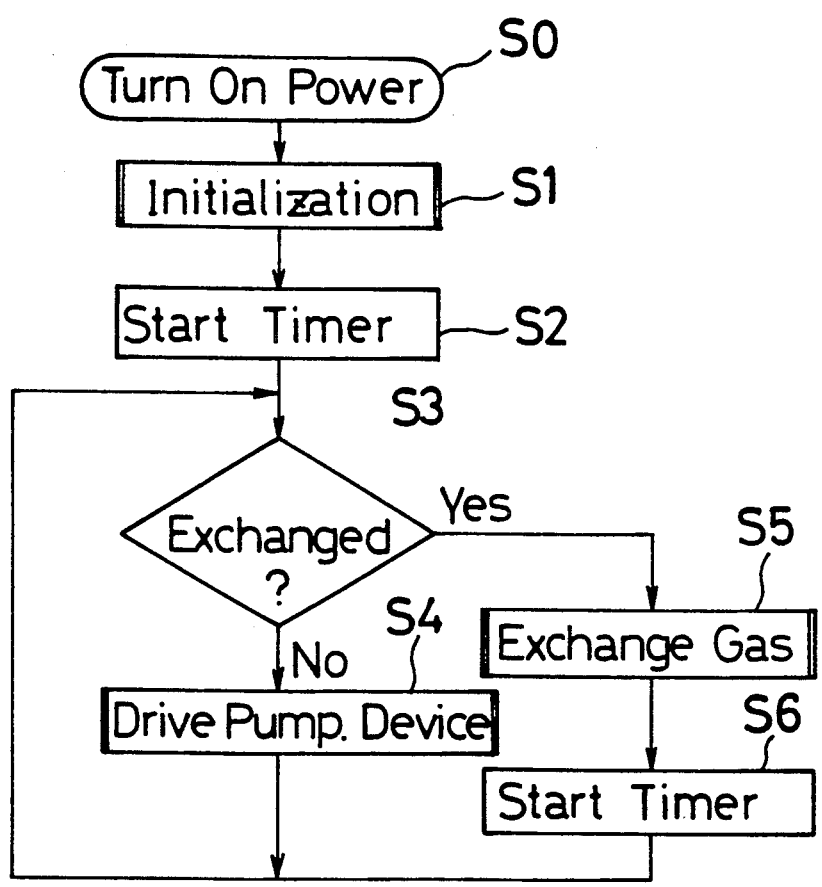
FIGS. 2a and 2b are flowcharts illustrating a computer program run by the electronic control unit of the apparatus shown in FIG. 1.

The operation of the electronic control unit 32 is described next by referring to the flowcharts of FIGS. 2a and 2b. Referring first to FIG. 2a, the power supply of the electronic control unit 32 is turned on (step 0). The unit 32 initializes various flags and input and output ports which are necessary for the subsequent processing (step 1). Then, the timer 35 is started to measure the time for which the pressure generator 31 operates (step 2). The unit 32 makes a decision based on the time measured by the timer 35 to see whether the shuttle gas should now be replaced (step 3). Whenever the pressure generator 31 drives the balloon pump 4 for about 2 hours, the unit 32 executes processing for exhanging helium (step 5). If the gas should not be replaced, the unit 32 drives the pump 4 to cure the patient 4 (step 4).

Figure 4:
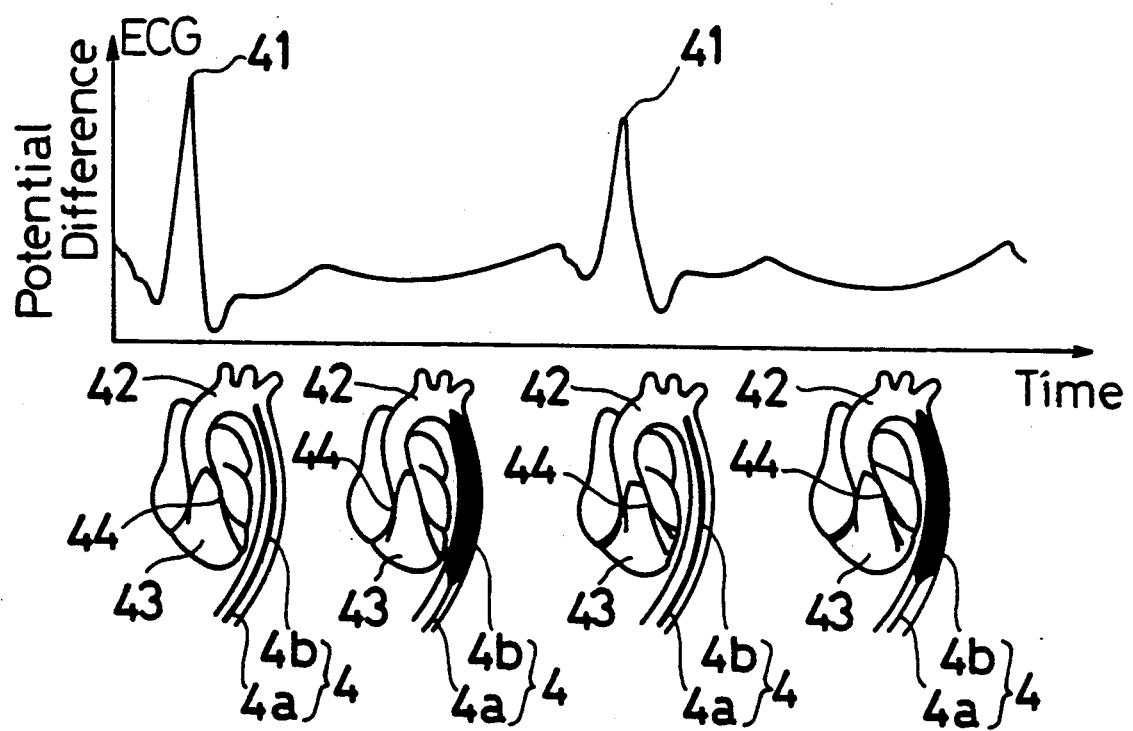
FIG. 4 is a diagram illustrating the relation of the waveform of an electrocardiogram to the expansion and contraction of a balloon pump.

The processing performed in step 4 for driving the blood-pumping device is now described. This processing has been already introduced by many papers and is known. Therefore, it is not described in detail herein. Only the fundamental operation is next described by referring to FIG. 4 which shows the relation of the waveform of an electrocardiogram to the expansion and contraction of the balloon pump 4.

The balloon pump 4 contracts immediately after R waves 41 are observed on the electrocardiogram, i.e., at the heart's systole. The contraction of the pump 4 reduces the pressure of blood in the base 42 of the aorta to permit the blood to be easily delivered from the cardiac ventricle 43 in a pulsatile manner. This increases the amount of flowing blood, thus helping the patient 1 recover. When a given time elapses after R waves were observed on the electrocardiogram, i.e., at the diastolic phase, the pump 4 is expanded. This increases the pressure of blood in the base 42 of the aorta. Hence, supply of oxygen and nutrition to the heart is promoted, which helps the weakened heart recover.

As described thus far, in step 4, the positive pressure-switching valve 313 and the negative pressure-switching valve 314 are alternately opened and closed according to the action of the heart detected by the electrocardiograph 33. The balloon pump 4 is made to expand and contract.

In the balloon portion 4b of the balloon pump 4, the shuttle gas is separated from the blood by a film of polyurethane. Therefore, the water vapor contained in the blood dissolves into the shuttle gas through the balloon portion 4b, thus increasing the mass of the shuttle gas. The water vapor dissolved in the shuttle gas changes into droplets of water, which hinder movement of the shuttle gas. As the shuttle gas contains more water vapor, the speeds at which the pump 4 contracts and expands drop. As a result, the pump 4 fails to contract and expand at the correct timing in response to the action of the heart.

In the present apparatus, the shuttle gas is replaced with new gas at regular intervals of time by referring to the timer 35, by taking account of the fact that the shuttle gas contains more water vapor with the lapse of time (step 5). The time interval is set so short that droplets of water are not yet produced from the water vapor increasing in the shuttle gas. In the present example, the time interval is set to about 2 hours. Since the amount of the water vapor contained in the shuttle gas is limited to a low ratio by replacing the shuttle gas with new gas, the rates at which the balloon pump 4 contracts and expands are kept substantially constant. After the completion of the exchange of the gas, the timer 35 is restarted (step 6), thus making preparations for the next exchange of the shuttle gas.

Figure 2B:
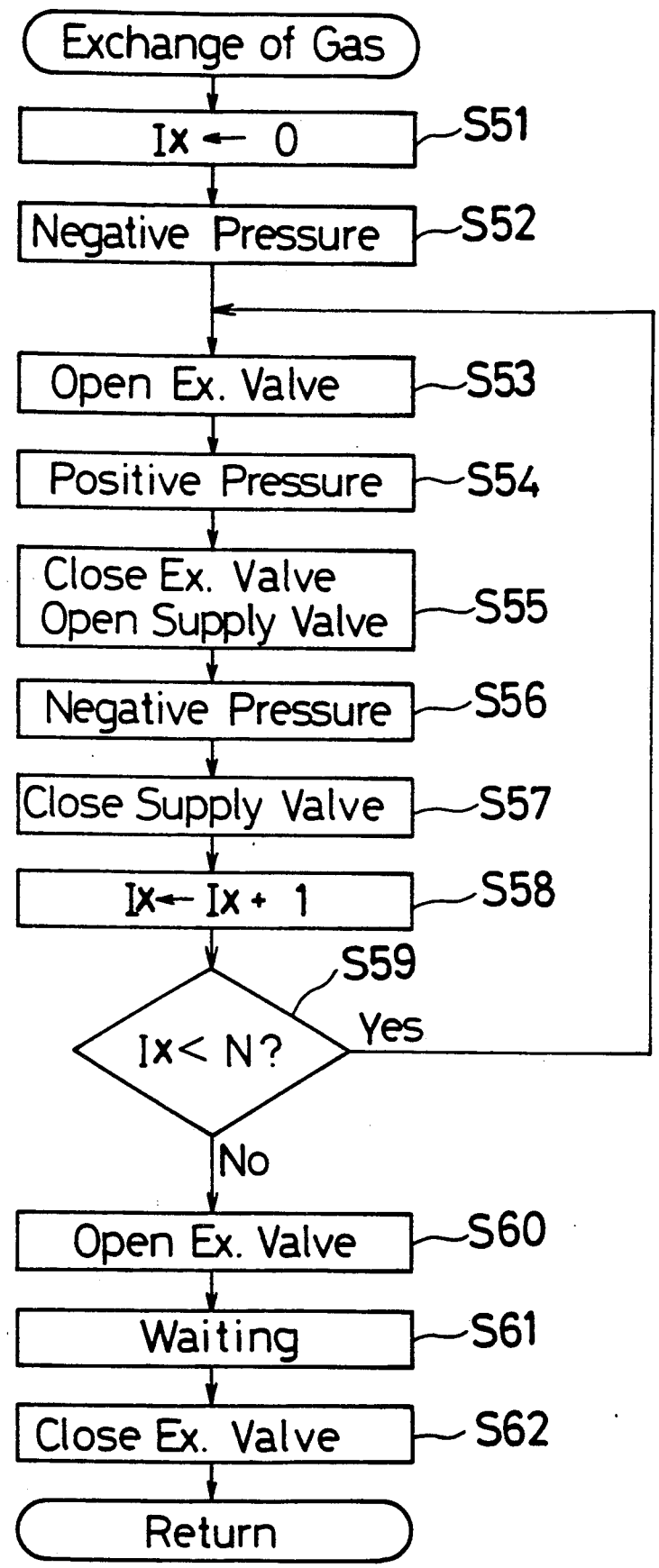

The processing (step 5) for exchanging the shuttle gas is next described in detail by referring to the flowchart of FIG. 2b. First, control flag 1 is set to zero (step 51). Control flag 1 is used to count the number of repetition of the exchange of the shuttle gas. Then, the electronic control unit 32 applies negative pressure to the isolator 315 (step 52) to cause the balloon pump 4 to contract, for the following purposes. The shuttle gas contained in the pump 4 is transferred into the secondary chamber 315c. When the gas is being exchanged, the pump 4 is prevented from coming to a halt while closing off the aorta.

After the balloon pump 4 contracts completely, the electronic control unit 32 opens the exhaust valve 341 (step 53). Thereafter, the unit 32 exerts positive pressure on the isolator 315 (step 54) to release the shuttle gas containing water vapor from the secondary chamber 315c into the atmosphere. A slight amount of water droplets may be produced in the secondary chamber 315c under some conditions, but the produced water droplets are discharged into the atmosphere together with the shuttle gas. At this time, the pressure inside the balloon pump 4 is maintained substantially at the atmospheric pressure and so the balloon portion 4a is retained contracted.

When the movable membrane 315b moves and the volume of the secondary chamber 315c decreases sufficiently, the electronic control unit 32 closes the exhaust valve 341 and opens the supply valve 342 (step 55). Then, new shuttle gas containing no water vapor flows into the secondary chamber 315c from the helium tank 343. At this time, the electronic control unit 32 causes negative pressure to act on the isolator 315 (step 56). This shifts the movable membrane 315b toward the primary chamber 315a to promote the suction of the shuttle gas into the secondary chamber 315c. When the volume of the secondary chamber 315c increases sufficiently, the electronic control unit 32 closes the supply valve 342 (step 57), thus completing one operation for exchanging the shuttle gas.

Almost all the shuttle gas in the secondary chamber 315c is exchanged with new gas by this operation. However, a slight amount of shuttle gas containing water vapor may remain in the balloon pump 4. For this reason, the electronic control unit 32 repeats this operation for exchanging the shuttle gas several times. As a result, the shuttle gas inside the pump 4 is exchanged with new gas with certainty.

The electronic control unit 32 counts the number of exchanges of the shuttle gas, using flag 1 (step 58). The exchange of the shuttle gas is repeated N times (step 59), where N is set according to the size of the pump 4. Normally, N is 2 or 3.

Subsequently, the electronic control unit 32 opens the exhaust valve 341 (step 60), and waits until the inside of the secondary chamber 315c reaches the atmospheric pressure (step 61). Then, the exhaust valve 341 is closed (step 62). Thus, the processing is completed.

As described thus far, in the present apparatus, the amount of the water vapor contained in the shuttle gas is determined by the use of the timer 35. The shuttle gas is exchanged with new gas each time a given time passes. Since the shuttle gas is automatically replaced with new gas when the amount of the water vapor in the shuttle gas increases, the increase in the mass of the shuttle gas is suppressed. Also, almost no water droplets are produced. Consequently, the novel apparatus can keep driving the blood-pumping device for a long time even if it is not monitored by a doctor or nurse.

In the above example, only the balloon pump 4 inserted in the aorta is used as a blood-pumping device. The invention can be applied directly to other blood-pumping devices such as the blood-pumping devices disclosed in Japanese Patent Publication No. 41800/1976, Japanese Patent Laid-Open Nos. 84562/1988 and 246173/1988.

In accordance with the present invention, as the amount of the water vapor contained in the shuttle gas is increased, the gas is exchanged with new gas. Therefore, the water vapor contained in the shuttle gas is limited to a slight amount. Hence, the increase in the amount of the shuttle gas is suppressed. Also, almost no water droplets are produced. In this way, removable of water which would have been heretofore done by a doctor or nurse is dispensed with.

What is claimed is:

1. An apparatus for driving a blood-pumping device, the apparatus comprising:
    an isolator having a primary chamber, a secondary chamber adapted to be connected to the blood-pumping device between which an amount of shuttle gas is filled, and a movable membrane separating the chambers from each other;
    a positive pressure source connected via a first switching valve to the primary chamber of the isolator;
    a negative pressure source connected via a second switching valve to the primary chamber of the isolator;
    an exhaust valve connected to the secondary chamber of the isolator;
    tank means for storing therein an amount of shuttle gas and connected via a supply valve to the secondary chamber;
    timer means for setting a predetermined period of time of operation; and
    control unit means set to control the switching valves for the positive pressure source and the negative pressure source, the exhaust valve, and the supply valve, such that after every predetermined period of time of operation of the blood-pumping device, the shuttle gas in the secondary chamber is exhausted and replaced a plurality of times prior to resumption of a next predetermined period of time.

2. The apparatus of claim 1, wherein the control unit means closes the exhaust valve while shuttle gas is delivered to the secondary chamber by the 3. The apparatus of claim 1, wherein the timer means is restarted after the shuttle gas is replaced a plurality of times.

4. The apparatus of claim 1, wherein the plurality of times is two or three.

5. The apparatus of claim 4, wherein the predetermined period of time is about two hours.

* * * * *

UNITED STATES PATENT AND TRADEMARK OFFICE
CERTIFICATE OF CORRECTION

PATENT NO. :  5,217,429
DATED      :  June 8, 1993
INVENTOR(S) :  Naritoshi KANAI It is certified that error appears in the above-indentified patent and that said Letters Patent is hereby corrected as shown below:

In Column 6, line 31, after "the" (second occurrence), insert
-- supply valve. --.

Signed and Sealed this

First Day of February, 1994

Attest:

BRUCE LEHMAN

*Attesting Officer*    Commissioner of Patents and Trademarks